United States Patent [19]

Chamberlin, Sr.

[11] Patent Number: Plant 5,873

[45] Date of Patent: Feb. 3, 1987

[54] PEACH TREE

[75] Inventor: Thomas O. Chamberlin, Sr., Visalia, Calif.

[73] Assignee: H.P. Metzler & Sons, Del Rey, Calif.

[21] Appl. No.: 715,735

[22] Filed: Mar. 25, 1985

[51] Int. Cl.[4] ..... A01H 5/03

[52] U.S. Cl. ..... Plt./43

[58] Field of Search ..... Plt./43

*Primary Examiner*—R. E. Bagwill

*Attorney, Agent, or Firm*—Worrel & Worrel

[57] ABSTRACT

A peach tree, denominated "June Sun", producing yellow fleshed, semi-cling fruit having a skin of bright red to yellow coloration tenacious to the flesh ripening for harvest about June 8 to June 10, when ungirdled.

1 Drawing Figure

BACKGROUND OF THE VARIETY

The present invention relates to a new and distinct variety of peach tree, denominated "June Sun", which responds very well to girdling and produces yellow fleshed, semi-cling fruit with skin tenacious to the flesh and of high red color ready for harvest about the fifth to the eighth of June in the San Joaquin Valley of California.

The commercial value of tree fruit is frequently directly related to how early in the season the fruit can be delivered to market. Thus, the earlier ripening varieties of tree fruit often are of the greatest commercial value. The "Spring Crest" peach tree is an example of a variety which is commercially successful, in part, because of its early ripening fruit.

However, early ripening varieties of peach tree commonly have characteristics which detract from their commercial appeal. The fruit of such varieties is normally of small size and therefore not as appealing. It has been known that by girdling such trees, not only can the date of ripening of the fruit be advanced up to a week, but the size of the fruit is also enhanced. Conversely, such girdling commonly causes a substantial increase in the percentage of splitting of the stones or pits of the fruit.

The variety of the present invention is distinct from such known varieties of peach tree in that it ripens early and responds well to girdling. Girdling advances the date of harvest to before that of the "Gem Free" peach tree, while if ungirdled the variety will be ready for harvest after the "Gem Free" peach tree. Furthermore, girdling of the instant variety does not seem to affect the holding quality or color of the fruit and splitting of the stones of the fruit, while virtually nonexistent if the trees are not girdled, is very minor where the trees are girdled.

ORIGIN AND ASEXUAL REPRODUCTION OF THE NEW VARIETY

The instant new variety of peach tree was discovered by me in 1978 and is a newly found seedling of the "June Lady" peach tree. Seeds of the June Lady peach tree were planted in a plot in the nursery of H. P. Metzler & Sons at 5286 South Del Rey Avenue, Del Rey, Calif. 93616 in 1975. The fruit of the present variety was observed in 1978 and its distinctive characteristics discovered at that time.

The new variety was asexually propagated under my direction at H. P. Metzler & Sons in 1978 by grafting several seedlings with scions from the newly discovered seedling. In the winter of 1979 the grafted seedlings were planted in a test nursery of H. P. Metzler & Sons at Del Rey, Calif. The seedlings of the new variety were observed in the nursery over several growing seasons and the tree and fruit characteristics resulting from such asexual reproduction proved to be identical to those of the original seedling of the new variety.

SUMMARY OF THE NEW VARIETY

The instant variety of peach tree is characterized by producing yellow fleshed, semi-cling fruit having a skin of bright red to yellow coloration tenacious to the flesh ready for harvest about June 8 to June 10 in the San Joaquin Valley of California when ungirdled and responding quite well to girdling by advancing the harvest date of the fruit several days without affecting the holding quality or color of the fruit and with only a very minor percentage of splitting of the stones thereof.

BRIEF DESCRIPTION OF THE DRAWING

The accompanying drawing is a color photograph of four mature fruit of the instant variety, one positioned to show the stem, a second positioned to show the apex, a third positioned to show the side having the suture and a fourth sliced along its longitudinal axis with the pit left in place. A representative twig is also shown in the photograph with characteristic leaves.

DETAILED DESCRIPTION

Referring more specifically to the pomological details of this new and distinct variety of peach tree, the following characteristics were observed under the ecological conditions prevailing at the nursery of H. P. Metzler & Sons at Del Rey, County of Fresno, State of California and is an outlined description thereof. All major color code plate identifications are by reference to the Color Name Chart of the Inter-Society Color Council, National Bureau of Standards.

TREE

Size: Normal size and very vigorous growth.

Productivity: Very good.

Regularity of bearing: Consistently bears well.

Trunk: Normal size with medium size lenticels, 10 to 12 per square inch and dark brown in color (62-d.g.y.Br.).

Branches: Normal size with medium size lenticels, 10 to 12 per square inch and dark brown in color (62-d.g.y.Br.).

Leaves:

*Length.*—6½ inches [16.51 cm] to 7 inches [17.78 cm].

*Width.*—1½ inches [3.81 cm] to 1¾ inches [4.445 cm].

*Shape.*—Lanceolate.

*Margin.*—Serrate.

*Color.*—Upper side (125 M 01G). Lower side (122-gy.YG.).

*Petiole.*—Approximately ⅜ inch [0.9525 cm] in length and ⅛ inch [0.3175 cm] in width.

*Stem glands.*—Reniform. Two of very small size opposed at base of leaf. Color (100 deep g.y.).

Flower buds:

*Size.*—Small ⅜ inch [0.9525 cm] in length and ¼ inch [0.635 cm] in diameter.

*Shape.*—Round and slightly elongated.

*Other distinguishing characteristics.*—Before petals open, the stamen are exposed ⅛ inch [0.3175 cm] to ¼ inch [0.635 cm], depending on stage of bud.

Flowers:

*Date of bloom.*—End of February to first of March. Generally about the time the "Spring Crest" peach tree blooms and possibly slightly before.

*Size.*—Small, ¼ inch [0.635 cm] in diameter and each petal 3/8 inch [0.9525 cm] in length.

*Color.*—Dark pink (#255 S.P.R.) outer edge with light pink (#247 s.p.PK.) center.

FRUIT

Maturity: Reached in Del Rey in the San Joaquin Valley of Calif. about June 5 to June 8 if girdled and about June 8 to June 10 if ungirdled, depending upon the weather.

Size: Diameter 2½ inches [6.35 cm] to 3 inches [7.62 cm]. Transverse dimension in suture plane 2½ inches [6.35 cm] to 3 inches [7.62 cm]. Transverse dimension in plane normal to suture plane 2½ inches [6.35 cm] to 3 inches [7.62 cm].

Form:

*Uniformity.*—Good.

*Symmetry.*—Good.

*Suture.*—Very smooth and light extending from base to apex about 3½ inches [8.89 cm].

*Ventral surface.*—Rounded to slightly flat.

*Stem cavity.*—Rounded and shallow, 5/16 inch [0.79375 cm] to ⅜ inch [0.9525 cm] in depth, ⅝ inch [1.5875 cm] to ¾ inch [1.905 cm] in width.

*Apex.*—Rounded to slightly flat.

*Base.*—Generaly flat and wide.

*Pistil point.*—Very small and slightly receded.

Stem:

*Size.*—Length 5/16 inch [0.79375 cm] and width 3/16 inch [0.47625 cm].

Skin:

*Thickness.*—Medium.

*Texture.*—Smooth, tough texture and tenacious to flesh.

*Tendency to crack.*—None.

*Pubescense.*—Light.

*Color.*—Very bright red (13 deep red) to yellow (83 brill yellow).

Flesh:

*Color.*—(83 brill yellow).

*Surface of pit cavity.*—(83 brill yellow).

*Aroma.*—Slight.

*Juice.*—Good, with good flavor for early peach.

*Flavor.*—Good. Taste is almost sweet with very little acid taste.

*Fibers.*—Not fiberous.

*Ripening.*—Even.

*Eating quality.*—Very firm with tight, smooth flesh. Good flavor.

Stone:

*Type.*—Not freestone.

*Fibers.*—None.

*Size.*—Length 1 5/16 inches [3.33375 cm], width 1 1/16 inches [2.69875 cm] and thickness 13/16 inch [2.06375 cm].

*Form.*—Normal peach pit with rough ridges running on longitudinal axes curving at apex. Slight ridge at base. Very small point at apex.

*Color.*—(89 p.y.).

*Ridges.*—Minor.

*Tendency to split.*—None. If tree is girdled, splitting is very minor (less than 3 percent).

Use: Fresh market.

*Keeping quality.*—Fruit will hold very well on tree and at least three weeks in storage.

*Shipping quality.*—Ships very well due to the skin being tough and tenacious to flesh and the flesh being very tight and of a non-melting type.

Although the new variety of peach tree possesses the described characteristics as a result of the growing conditions in Fresno County, Calif., in the central portion of the San Joaquin Valley, it is to be understood that variations of the usual magnitude and characteristics incident to growing conditions, fertilization, pruning, pest control and other horticultural practices are to be expected.

Having thus described and illustrated my new variety of peach tree, what is claimed as new and desired to be secured by Letters Patent is:

1. A new and distinct variety of peach tree substantially as illustrated and described and which is characterized by producing yellow fleshed, semi-cling fruit having a skin of bright red to yellow coloration tenacious to the flesh ripening for harvest about June 8 to June 10 when ungirdled and responding well to girdling by advancing the harvest date of the fruit several days with only a very minor percentage of splitting of the stones of the fruit.

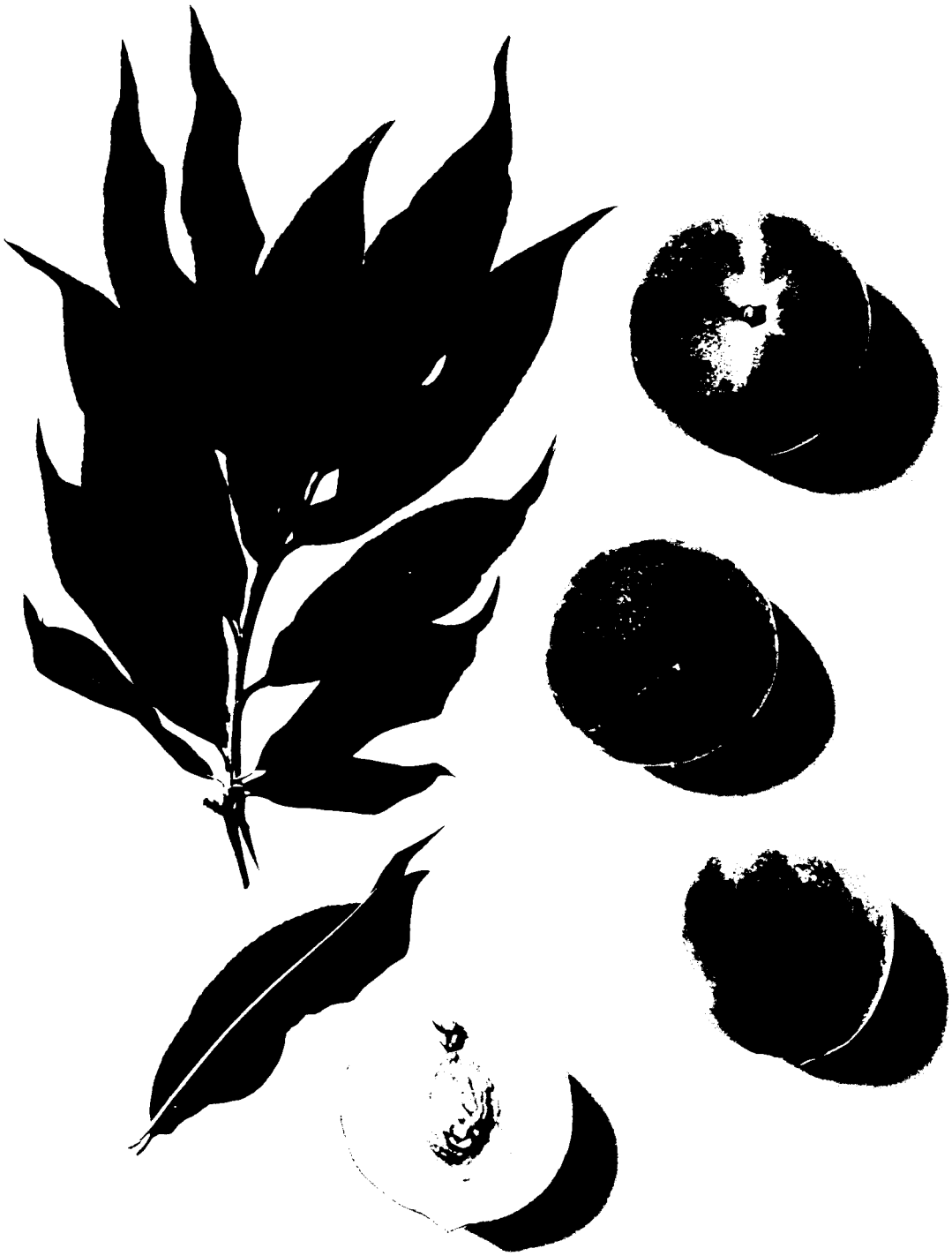

* * * * *